_United States Patent_ [19]

Saji et al.

[11] Patent Number: 4,526,983

[45] Date of Patent: Jul. 2, 1985

[54] PROCESS FOR PREPARING OPTICALLY ACTIVE IMIDAZOLYLPROPANOL COMPOUNDS, AND INTERMEDIATE THEREIN

[75] Inventors: Ikutaro Saji, Suita; Renzo Sato, Takarazuka; Noritaka Hanma, Sakai; Yasuo Motoike, Minoo, all of Japan

[73] Assignee: Sumitomo Chemical Company, Limited, Osaka, Japan

[21] Appl. No.: 497,579

[22] Filed: May 24, 1983

[51] Int. Cl.³ .......................................... C07D 233/54
[52] U.S. Cl. ................................................... 548/341
[58] Field of Search ......................... 548/341; 424/273

[56] References Cited

FOREIGN PATENT DOCUMENTS 0023103  1/1981  European Pat. Off. ............ 548/341
0054974  6/1982  European Pat. Off. ............ 548/341
  12372  of 1981  Japan ................................... 548/341
 106666  of 1982  Japan ................................... 548/341

OTHER PUBLICATIONS

Morrison, R. and Boyd, R., Textbook of Org. Chem., 6/78, pp. 236 and 237.
Journal of Syn. Org. Chem., Japan, 38, pp. 1151-1162, 1980.
Org. Chem., Col, vol. III, p. 116.
J. Syn. Org. Chem.—Chemistry and Actions of the Recent Synthetic Pyrethroids and Their Stereoisomers.

_Primary Examiner_—Henry R. Jiles
_Assistant Examiner_—J. G. Mullins
_Attorney, Agent, or Firm_—Birch, Stewart, Kolasch & Birch

[57] ABSTRACT

An optically active imidazolylpropanol compound of the formula:

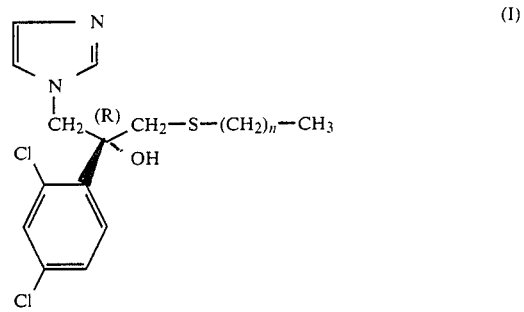

(I)

wherein n is an integer of 3 or 4, and its acid addition salts, which is useful as an antifungal agent, prepared by reacting an imidazolylthiol of the formula:

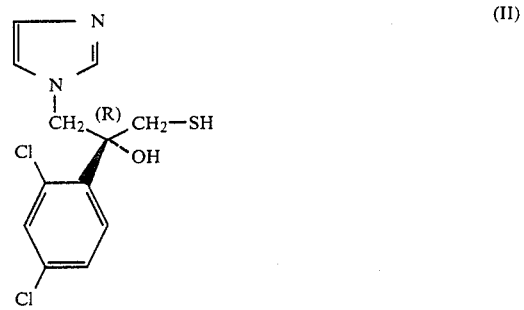

(II)

with an alkylating agent of the formula:

$$CH_3-(CH_2)_n-X \quad \quad (III)$$

wherein n is as defined above and X is a halogen atom, an alkylsulfonyloxy group or an arylsulfonyloxy group.

11 Claims, No Drawings

PROCESS FOR PREPARING OPTICALLY ACTIVE IMIDAZOLYLPROPANOL COMPOUNDS, AND INTERMEDIATE THEREIN

The present invention relates to a process for preparing optically active imidazolylpropanol compounds, and an intermediate in the production thereof.

The said optically active imidazolylpropanol compounds are representable by the formula:

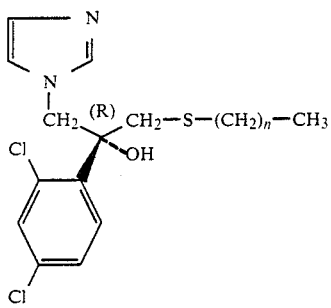
(I)

wherein n is an integer of 3 or 4.

The racemic mixture of an imidazolylpropanol compound corresponding to the formula (I) is known to be useful as an antifungal agent (cf. Japanese Patent Publication (unexamined) No. 106666/1982). In order to provide more active compounds, an extensive study has been made, and it has been found that the (R)-isomer of the imidazolylpropanol compound (I) is highly active.

On Candida infection in mice, the said (R)-isomer showed a more remarkable effect in decreasing mortality than the corresponding racemate or (S)-isomer. Thus, the (R)-isomer is particularly useful as an antifungal agent.

The present invention provides a novel process for preparing the optically active imidazolylpropanol compounds of the formula (I), i.e. the (R)-isomer, which may be illustratively shown in the following scheme:

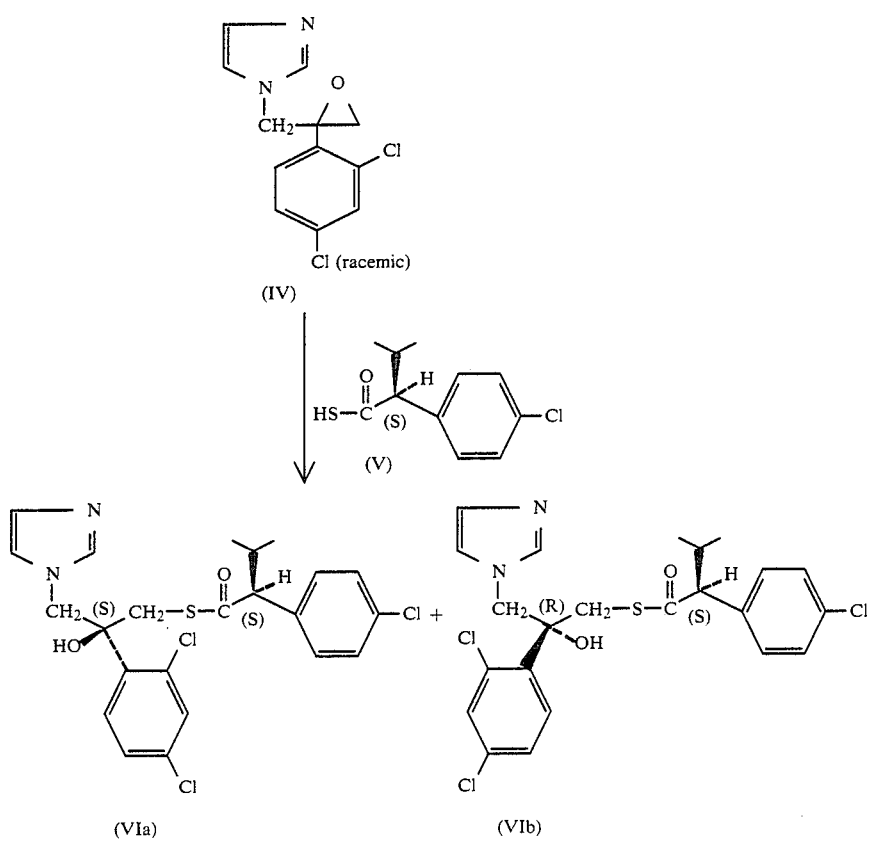

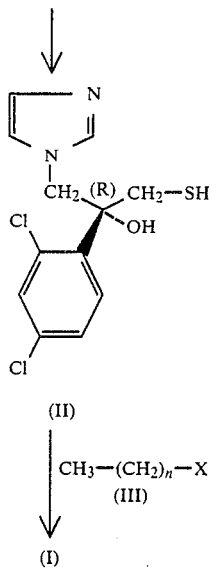

(II)

$$\Big| \quad CH_3-(CH_2)_n-X \quad (III)$$

(I)

In the above method, the racemic epoxide of the formula (IV) is first reacted with an optically active thiolocarboxylic acid of the formula (V) in an inert solvent at a temperature of from about −20° to 80° C. to give a 1:1 diastereomeric mixture of the thioloesters (VIa) and (VIb).

The racemic epoxide (VI) is known (cf. Japanese Patent Publications (unexamined) Nos. 12372/1981 and 106666/1982). The optically active thiolocarboxylic acid (V) can be prepared from the corresponding carboxylic acid chloride of the formula:

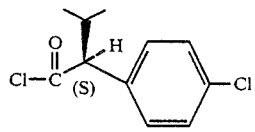

(J. Synthetic Organic Chemistry, Japan, 38, 1151–1162 (1980)) by reacting the latter with potassium or sodium hydrosulfide in an inert solvent such as a hydrocarbon (e.g. benzene, toluene) or an alcohol (e.g. methanol, ethanol) at a temperature of about −10° to 10° C. (cf. Org. Synthesis, Col. Vol. III, p. 116). The optically active thiolocarboxylic acid (V) is merely a typical example, and other optically active thiolocarboxylic acids such as (+)-α-methoxy-α-trifluoromethylphenyl-thioloacetic acid and L-menthoxythioloacetic acid may be also used. These optically active thiolocarboxylic acids are representable by the formula: A-SH wherein A is an optically active acyl group. Examples of the inert solvent are hydrocarbons (e.g. n-hexane, benzene, xylene), alcohols (e.g. methanol, ethanol, isopropanol), halogenated hydrocarbons (e.g. dichloromethane, chloroform, 1,2-dichloroethane), ketones (e.g. acetone, methyl ethyl ketone), ethers (e.g. diethyl ether, tetrahydrofuran, dioxane), esters (e.g. ethyl acetate), amides (e.g. N,N-dimethylformamide, N,N-dimethylacetamide), etc. The amount of the optically active thiolocarboxylic acid (V) may be usually a molar equivalent or slightly excess to the racemic epoxide (IV).

From the 1:1 diastereomeric mixture, the (R)-isomer (VIb) is separated and collected by a per se conventional separation procedure such as fractional crystallization. For the fractional crystallization, an inert solvent such as an alcohol (e.g. methanol, ethanol, isopropanol) or a hydrocarbon (e.g. n-hexane, benzene, toluene, xylene) may be used.

The most straightforward procedure for obtaining the desired (R)-isomer (VIb) comprises performing the reaction between the racemic epoxide (IV) and the optically active thiolocarboxylic acid (V) in a solvent usable for the fractional crystallization. In such case, the crystals of the (R)-isomer are separated out from the reaction system on the completion of the reaction and can be readily collected by filtration.

The separated (R)-isomer (VIb) is then treated with a base in an inert solvent at a temperature of about −10° to 100° C. in an inert atmosphere (e.g. nitrogen, argon) to give the imidazolylthiol of the formula (II). As the base, there may be used an alkali metal hydroxide (e.g. lithium hydroxide, sodium hydroxide, potassium hydroxide), an alkali metal carbonate (e.g. sodium carbonate, potassium carbonate), an alkali metal alcoholate (e.g. sodium ethylate, sodium methylate), an alkali metal sulfhydrate (e.g. sodium sulfhydrate, potassium sulfhydrate), ammonia, organic amines (e.g. monomethylamine, diethylamine, triethylamine), etc. Examples of the inert solvent are water, alcohols (e.g. methanol, ethanol, isopropanol), ketones (e.g. acetone, methyl ethyl ketone), ethers (diethyl ether, tetrahydrofuran, dioxane), amides (e.g. N,N-dimethylformamide, N,N-dimethylacetamide), etc. Mixtures of the above bases can also be used. The amount of the base is usually not less than 1 mole, preferably from 1 to 20 moles, per mole of the (R)-isomer (VIb).

Then, the imidazolylthiol (II) is reacted with an alkylating agent of the formula (III), preferably in the presence of a base in an inert solvent to give the objective optically active imidazolylpropanol compound (I). In the formula (III) for the alkylating agent, X represents a halogen atom (e.g. chlorine, bromine, iodine), an alkylsulfonyloxy group (e.g. methanesulfonyloxy) or an arylsulfonyloxy group (e.g. benzenesulfonyloxy, toluenesulfonyloxy). Examples of the base are an alkali metal hydroxide (e.g. lithium hydroxide, sodium hydroxide, potassium hydroxide), an alkali metal carbonate (e.g. sodium carbonate, potassium carbonate), an alkali metal (e.g. lithium, sodium, potassium), and alkali metal hydride (e.g. sodium hydride), a tertiary amine (e.g. pyridine, triethylamine), etc. As the inert solvent, there may be used a hydrocarbon (e.g. benzene, toluene, xylene), a chlorinated hydrocarbon (e.g. methylene chloride, chloroform, 1,2-dichloroethane), an alcohol (e.g. methanol, ethanol, isopropanol), a ketone (e.g. acetone, methyl ethyl ketone), an ether (e.g. diethyl ether, tetrahydrofuran, dioxane), an ester (e.g. ethyl acetate), an amide (e.g. N,N-dimethylformamide, N,N-dimethylacetamide), water, etc. The amount of the alkylating agent (III) may be more than 1 mole, preferably 1 to 10 moles, per mole of the imidazolylthiol (II). The amount of the base is usually more than 1 mole, preferably 1 to 30 moles, per mole of the imidazolylthiol (II). The reaction temperature is usually above $-20°$ C., preferably from $-20°$ to 100° C.

The optically active imidazolylpropanol compound (I) can be prepared more conveniently and advantageously by treating the (R)-isomer (VIb) successively with the base and with the alkylating agent (III) in a single reaction vessel without isolation of the intermediarily produced imidazolylthiol (II).

The manner for recovery of the optically active imidazolylpropanol compound (I) from the reaction mixture depends upon the properties of the reactants utilized but in general, the reaction mixture is subjected to evaporation of the solvent, dilution of the residue with water and extraction of the objective optically active imidazolylpropanol compound (I) with an appropriate water-immiscible solvent.

The thus produced optically active imidazolylpropanol compound (I) may be converted into its acid addition salt by treatment with an acid (e.g. hydrochloric acid, hydrobromic acid, phosphoric acid, nitric acid, acetic acid, maleic acid, succinic acid, fumaric acid, tartaric acid, citric acid, salicylic acid, sorbic acid, lactic acid, oxalic acid).

The optically active imidazolylpropanol compounds of the formula (I) are usually administered to patients orally or parenterally and are ordinarily employed in the form of a pharmaceutical composition which contains them in an effective and non-toxic amount in admixture with conventional pharmaceutical carrier materials suitable for oral or parenteral application and being unreactive with the active compounds. The pharmaceutical composition may be in the dosage form of tablets, capsules, granules, fine granules, powders, syrups, suspensions, emulsions, suppositories, injections, or the like. These pharmaceutical compositions can be prepared by conventional methods by using conventional carrier materials, excipients, binding agents, stabilizers, etc. For injection, the preparation may be prepared by dissolving the active compounds in purified water for injection, which may optionally contain other additives, such as isotonic agents (e.g. glucose, saline), buffering agents, solubilizers, pH adjusting agents or preservatives.

The dosage of the optically active imidazolylpropanol compounds (I) may vary with the administration routes, the age and weight of the patient, the kinds and severity of the diseases to be treated, or the like. In case of oral administration in adult, it is usually used in an amount of 50 to 1,000 mg, preferably of 100 to 500 mg, per day, which may be administered once a day but may also be divided and administered in two to several times per day. In case of injection in adult, it is usually used in an amount of 10 to 400 mg, preferably 20 to 200 mg, per day, which may be administered once a day but may also be divided and administered in two to several times per day.

Practical and presently preferred embodiments for production of the compounds (I) are illustratively shown in the following Examples.

EXAMPLE 1

Preparation of (R)-3-[(S)-2-(4-chlorophenyl)isovalerylthio]-2-(2,4-dichlorophenyl)-1-(imidazol-1-yl)-2-propanol (VIb)

To a solution of dl-2-(2,4-dichlorophenyl)-2-(imidazol-1-yl)methyloxirane (IV) (269 g) in toluene (1100 ml) was added (S)-2-(4-chlorophenyl)thioloisovaleric acid (V) (229 g) obtained in Reference Example 5 at room temperature. The mixture was stirred without external cooling, while the temperature raised spontaneously to 55° C. during the first 10 minutes. The mixture was kept at the same temperature as above for another 1 hour and then at 20° C. for 3 hours. The precipitate was collected by filtration, washed successively with toluene and isopropanol and dried in vacuo to give (R)-3-[(S)-2-(4-chlorophenyl)isovalerylthio]-2-(2,4-dichlorophenyl)-1-(imidazol-b 1-yl)-2-propanol (VIb) (204 g). Yield, 41%. M.P., 182°–183° C. $[\alpha]_D^{23} -1.0°$ (c=1, methanol).

EXAMPLE 2

Preparation of (R)-2-(2,4-dichlorophenyl)-1-(imidazol-1-yl)-3-mercapto-2-propanol (II)

To a suspension of the compound (VIb) (49.5 g) obtained in Example 1 in toluene (300 ml) was added a 10% methanolic potassium hydroxide solution (160 g) at a temperature of $-5°$ C. to 0° C. in nitrogen atmosphere. The mixture was warmed to 25° C. over a period of about 30 minutes and stirred at the same temperature for 2 hours. The reaction mixture was concentrated under reduced pressure. The residue was dissolved in dichloromethane (300 ml), washed with water, dried and evaporated to give an oil. The oil was purified by silica gel column chromatography using chloroform as an eluent and recrystallized from a mixture of dichloromethane and n-hexane to give (R)-2-(2,4-dichlorophenyl)-1-(imidazol-1-yl)-3-mercapto-2-propanol (II) (9.4 g). Yield, 31%.. M.P., 155°–157° C. $[\alpha]_D^{24} -6.6°$ (c=1, methanol).

EXAMPLE 3

Preparation of (R)-2-(2,4-dichlorophenyl)-1-(imidazol-1-yl)-3-mercapto-2-propanol (II)

In the same manner as in Example 2 but using 10% water-containing methanol (400 ml) and sodium sulfhydrate (10 g) in place of methanol and potassium hydroxide, respectively, there was obtained (R)-2-(2,4-dichlorophenyl)-1-(imidazol-1-yl)-3-mercapto-2-propanol (II) (11.3 g). Yield, 37%. M.P., 156°–157° C. $[\alpha]_D^{24} -7.0°$ (c=1, methanol).

EXAMPLE 4

Preparation of (R)-3-(n-butylthio)-2-(2,4-dichlorophenyl)-1-(imidazol-1-yl)-2-propanol (I: n=3) hydrochloride To a solution of sodium hydroxide (2 g) in methanol (100 ml) were added n-butylbromide (2 g) and (R)-2-(2,4-dichlorophenyl)-1-(imidazol-1-yl)-3-mercapto-2-propanol (II) obtained in Example 2 at a temperature of 20°–25° C. in nitrogen atmosphere. The mixture was stirred at 25°–30° C. for 5 hours and then concentrated under reduced pressure. The residue was treated with water (50 ml) and extracted with dichloromethane (50 ml). The extract was washed with water, dried over anhydrous magnesium sulfate and concentrated to give an oil. The oil was dissolved in diethyl ether (20 ml), and hydrogen chloride gas was introduced thereto. Precipitated crystals were collected by filtration and dried to give (R)-3-(n-butylthio)-2-(2,4-dichlorophenyl)-1-(imidazol-1-yl)-2-propanol (I: n=3) hydrochloride (3.4 g). Yield, 86.8%. M.P., 168°–169° C. $[\alpha]_D^{20} -89.7°$ (c=1, methanol). The optical purity of the product was not less than 99% determined by high performance liquid chromatography.

EXAMPLE 5

Preparation of (R)-3-(n-butylthio)-2-(2,4-dichlorophenyl)-1-(imidazol-1-yl)-2-propanol (I: n=3) hydrochloride To a solution of (R)-2-(2,4-dichlorophenyl)-1-(imidazol-1-yl)-3-mercapto-2-propanol (II) (3 g) in dry N,N-dimethylformamide (20 ml) were added a 50% dispersion of sodium hydride in paraffin (1 g) and n-butyl p-toluenesulfonate (2.3 g) at 0°–5° C. in nitrogen atmosphere. The mixture was stirred at 0°–5° C. for 1 hour and at 20°–25° C. for 18 hours. The reaction mixture was diluted with water (200 ml) and extracted with dichloromethane. Treatment of the extract in the same manner as in Example 4 gave (R)-3-(n-butylthio)-2-(2,4-dichlorophenyl)-1-(imidazol-1-yl)-2-propanol (I: n=3) hydrochloride (2.5 g). Yield, 63.8%. M.P., 168°–169° C. $[\alpha]_D^{20} -88.8°$ (c=1, methanol).

EXAMPLE 6

Preparation of (R)-3-(n-butylthio)-2-(2,4-dichlorophenyl)-1-(imidazol-1-yl)-2-propanol (I: n=3) hydrochloride To a suspension of (R)-3-[(S)-2-(4-chlorophenyl)isovalerylthio]-2-(2,4-dichlorophenyl)-1-(imidazol-1-yl)-2-propanol (VIb) (49.5 g) obtained in Example 1 in methanol (500 ml) were added a 10% methanolic potassium hydroxide solution (240 g) and n-butylbromide (21.6 g) at −5° to 0° C. in nitrogen atmosphere. The slurry was stirred at the same temperature for 2 hours and then at 30° C. for 3 hours. Methanol was removed by distillation under atmospheric pressure, and the residue was treated with water (200 ml) and extracted with 1,2-dichloroethane (200 ml). The extract was washed successively with water and 12% hydrochloric acid (200 ml) and concentrated in vacuo. To the residue were added toluene (100 ml) and methyl ethyl ketone (35 ml), and the slurry was stirred at 15° C. for 3 hours. Filtration and drying in vacuo gave a crude product (25.7 g), which was recrystallized from methyl ethyl ketone to give (R)-3-(n-butylthio)-2-(2,4-dichlorophenyl)-1-(imidazol-1-yl)-2-propanol (I: n=3) hydrochloride (21.8 g) as colorless needles. Yield, 55%. M.P., 168.5°–170° C. $[\alpha]_D^{20} -89.8°$ (c=1, methanol).

REFERENCE EXAMPLE 1

Preparation of (S)-2-(4-chlorophenyl)thioloisovaleric acid (V)

To a solution of potassium hydroxide (296 g) in methanol (1500 ml) was introduced hydrogen sulfide gas (180 g) from a gas-inlet tube at a temperature below 30° C., and the mixture was cooled at −5° C. A solution of (S)-2-(4-chlorophenyl)isovaleryl chloride (510 g) in toluene (1000 ml) was dropwise added thereto at a temperature of −5° to 10° C. The mixture was stirred at the same temperature for 30 minutes, followed by addition of water (2000 ml). A 35% hydrochloric acid (455 g) was dropwise added thereto. The toluene layer was washed with water (500 ml) and concentrated in vacuo to give (S)-2-(4-chlorophenyl)thioloisovaleric acid (V) (504 g), which was used for the reaction in Example 1 without purification.

The optically active imidazolylpropanols (I) exhibit a remarkable antimicrobial activity against various microorganisms, particularly fungi. Also, some of them show an antifungal activity against phytopathogenic fungi.

Advantageously, the optically active imidazolylpropanol compounds (I) are quite low in toxicity, and their $LD_{50}$ values are more than 500 mg/kg when determined by oral route to mice. Thus, they are useful as antifungal agents.

The optically active imidazolylpropanol compounds (I) can be administered parenterally, orally or locally to warm-blooded animals and human beings in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 10 mg and 5 g for human beings.

What is claimed is:

1. An imidazolylthiol of the formula:

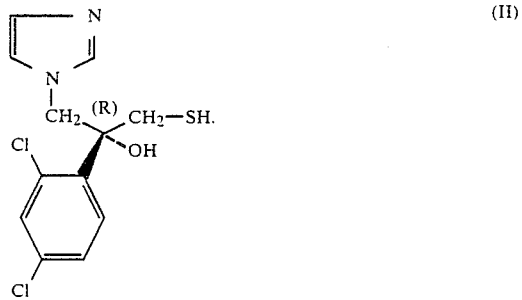

2. A process for preparing optically active imidazolylpropanol compounds of the formula:

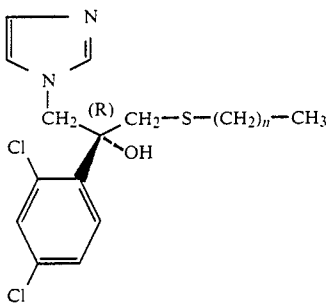 (I)

wherein n is an integer of 3 or 4, and their acid addition salts, which comprises:

(1) reacting a racemic expoxide of the formula:

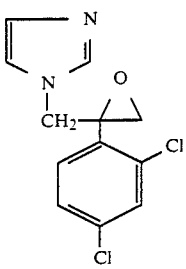 (IV)

with an optically active thiolocarboxylic acid of the formula

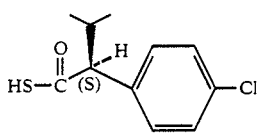 (V)

to give a mixture of two diastereomeric isomers of the formulas:

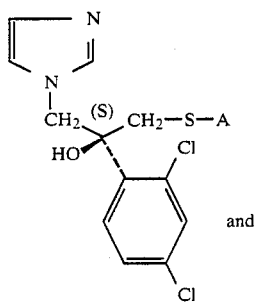 (VIa)

and

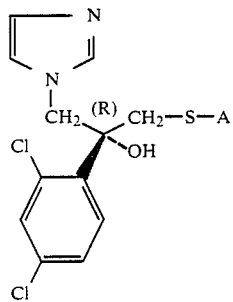 (VIb)

wherein A is as defined above;
(2) separating the (R)-isomer from said mixture; and
(3) reacting the (R)-isomer with a base to give an imidazolylthiol of the formula:

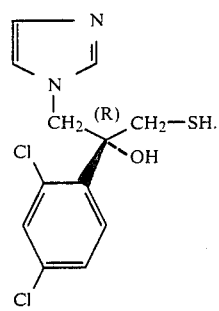 (II)

3. The process according to claim 1, wherein said racemic epoxide of the formula (IV) is reacted with said optically active thiolocarboxylic acid in an inert solvent at about −20° to 80° C.

4. The process according to claim 2, wherein said racemic epoxide of the formula (IV) is reacted with said optically active thiolocarboxylic acid in an inert solvent at about −20° to 80° C.

5. The process according to claim 1, wherein in step (3) said (R)-isomer is reacted with a base in an inert solvent at a temperature of about −10° to 100° C. in an inert atmosphere, and said base is a member selected from alkali metal hydroxides, alkali metal carbonates, alkali metal sulfhydrates, ammonia and organic amines, or mixtures thereof.

6. The process according to claim 5, wherein said base is utilized in an amount of from 1 to 20 moles per mole of said R-isomer (VIb).

7. The process according to claim 2, wherein in step (3) said (R)-isomer is reacted with a base in an inert solvent at a temperature of about −10° to 100° C. in an inert atmosphere, and said base is a member selected from alkali metal hydroxides, alkali metal sulfhydrates, ammonia and organic amines, or mixtures thereof.

8. The process according to claim 7, wherein said base is utilized in amount of from 1 to 20 moles per mole of said R-isomer (VIb).

9. A process for preparing optically active imidazolylpropanol compounds of the formula:

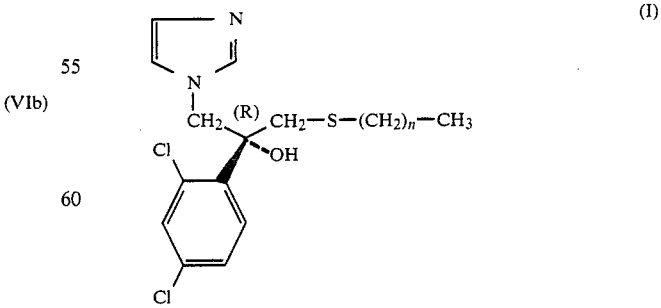 (I)

wherein n is an integer of 3 or 4, and their acid addition salts, which consists essentially of:

(1) reacting a racemic epoxide of the formula:

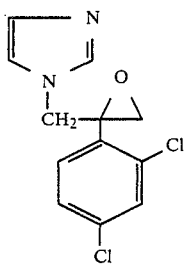

with an optically active thiolocarboxylic acid of the formula:

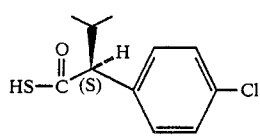

to give a mixture of two diastereomeric isomers of the formulas:

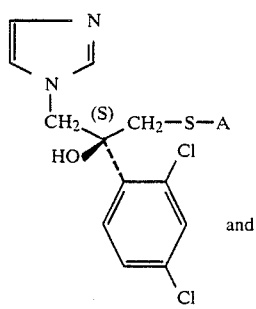

and

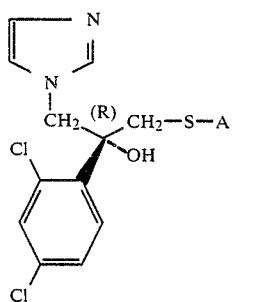

wherein A is as defined above;
(2) separating the (R)-isomer from said mixture; and
(3) reacting the (R)-isomer with a base and alkylating agent of the formula:

$$CH_3—(CH_2)_n—X \qquad (III)$$

wherein n is as defined above and X is a halogen atom, an alkylsulfonyloxy group or an arylsulfonyloxy group.

10. A process according to claim 9, wherein said base is a member selected from the group consisting of alkali metal hydroxides, alkali metal carbonates, alkali metal sulfhydrates, ammonia and organic amines, or mixtures thereof.

11. A process for preparing optically active imidazolylpropanol compounds of the formula:

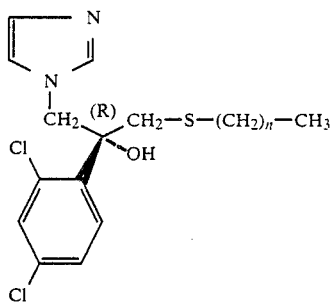

wherein n is an integer of 3 or 4, and their acid addition salts, which comprises:
(1) reacting a racemic epoxide of the formula:

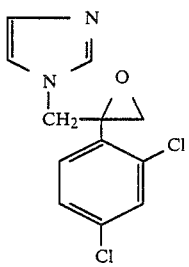

with an optically active thiolocarboxylic acid of the formula:

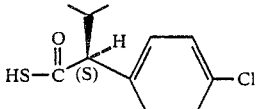

to give a mixture of two diastereomeric isomers of the formulas:

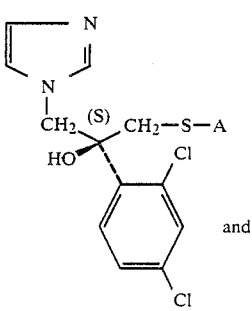

and

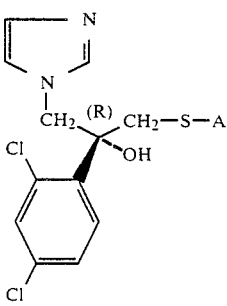

wherein A is as defined above;
(2) separating the (R)-isomer from said mixture;
(3) reacting the (R)-isomer with a base to give an imidazolylthiol of the formula:
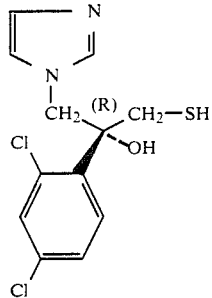
(II)
and
(4) reacting the imidazolylthiol with an alkylating agent of the formula:
(III)
wherein n is as defined above and X is a halogen atom, an alkylsulfonyloxy group or an arylsulfonyloxy group.
* * * * *

UNITED STATES PATENT AND TRADEMARK OFFICE
CERTIFICATE OF CORRECTION

PATENT NO. : 4,526,983

DATED : July 2, 1985

INVENTOR(S) : I. Saji, R. Sato, N. Hanma, Y. Motoike

It is certified that error appears in the above-identified patent and that said Letters Patent is hereby corrected as shown below:

In The Claims:

Claim 2, column 9, change formula (I) to read

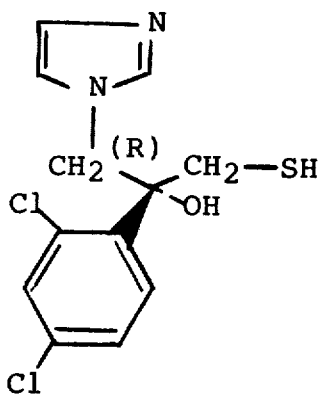

column 10, line 1, change "as defined above" to read --a group of the formula:

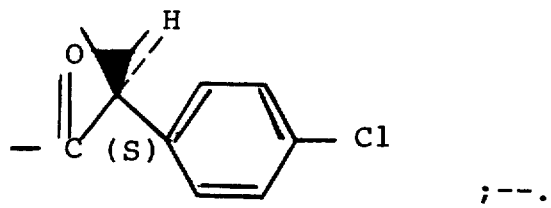

;--.

Claim 3, column 10, line 20, change dependency from "1" to --2--.

Claim 5, column 10, line 28, change dependency from "1" to --11--.

Claim 6, column 10, line 36, change dependency from "5" to --11--.

UNITED STATES PATENT AND TRADEMARK OFFICE
CERTIFICATE OF CORRECTION

PATENT NO. : 4,526,983
DATED : July 2, 1985
INVENTOR(S) : I. Saji, R. Sato, N. Hanma, Y. Motoike It is certified that error appears in the above-identified patent and that said Letters Patent is hereby corrected as shown below:

<u>Claim 8</u>, column 10, line 46, change dependency from "7" to --2--.
<u>Claim 9</u>, column 11, line 54, after "and" insert --an--.
<u>Claim 11</u>, column 13, line 1, change "as defined above" to read --a group of the formula:

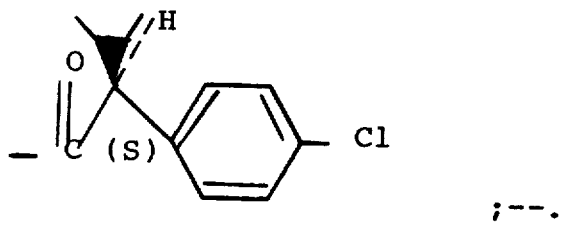

;--.

Signed and Sealed this

Eighteenth Day of March 1986

[SEAL]

Attest:

DONALD J. QUIGG

Attesting Officer

Commissioner of Patents and Trademarks